United States Patent
Mauze et al.

(10) Patent No.: US 7,049,129 B2
(45) Date of Patent: May 23, 2006

(54) ELECTRO-OPTICAL DEVICES AND METHODS FOR HYBRIDIZATION AND DETECTION

(75) Inventors: Ganapati R. Mauze, Sunnyvale, CA (US); Dan-Hui Yang, Sunnyvale, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 10/414,719

(22) Filed: Apr. 15, 2003

(65) Prior Publication Data

US 2004/0018612 A1    Jan. 29, 2004

Related U.S. Application Data

(62) Division of application No. 09/848,869, filed on May 4, 2001.

(51) Int. Cl.
| | |
|---|---|
| C12M 1/34 | (2006.01) |
| C12Q 1/68 | (2006.01) |
| G01N 33/20 | (2006.01) |
| G01N 33/00 | (2006.01) |

(52) U.S. Cl. ............... 435/287.2; 435/6; 435/810; 436/73; 436/94; 436/182; 536/23.1; 536/24.3; 536/25.32

(58) Field of Classification Search ............ 435/6, 435/91.1, 183, 287.2; 436/94, 800, 805, 436/806, 172; 536/23.1, 24.3
See application file for complete search history.

(56) References Cited

U.S. PATENT DOCUMENTS

| | | | |
|---|---|---|---|
| 5,591,578 A | 1/1997 | Meade et al. | |
| 5,686,244 A | 11/1997 | Gudibande et al. | |
| 5,714,089 A | 2/1998 | Bard et al. | |
| 5,945,344 A | 8/1999 | Hayes et al. | |
| 5,952,172 A * | 9/1999 | Meade et al. | 435/6 |
| 6,048,687 A | 4/2000 | Kenten et al. | |
| 6,140,138 A | 10/2000 | Bard et al. | |

FOREIGN PATENT DOCUMENTS

WO    WO 99/31115    6/1999

* cited by examiner

*Primary Examiner*—Bradley L. Sisson

(57) ABSTRACT

The invention provides an apparatus and method for detection of a target molecule. The apparatus includes a probe labeled with a transition metal-ligand complex that hybridizes with the target to form an initial complex, a metal ion for doping the initial complex and forming a final complex, and a potential means for providing a potential to the final complex to produce a detectable signal indicating the presence of the target after redox reaction. The method of the invention teaches the steps of hybridizing a probe with an attached label to the target to produce an initial complex, adding a metal ion to the initial complex to form a final complex and applying a potential to the final complex to produce a measurable signal.

15 Claims, 6 Drawing Sheets

ELECTRO-OPTICAL DEVICES AND METHODS FOR HYBRIDIZATION AND DETECTION

TECHNICAL FIELD OF THE INVENTION

The invention relates to the field of nucleic acids and more particularly to the detection of presence of or a change in sequence or structure based on hybridized probes.

BACKGROUND OF THE INVENTION

A number of techniques are known and have been developed for detecting the presence of nucleic acids and their structural changes. However, most of these techniques chemically alter the nucleic acid of interest or change the molecule in some fashion. For instance, modification of DNA sequences has been accomplished using restriction enzymes. These enzymes digest the nucleic acid into defined sequences and alter the defined order or continuity of the molecule. Restriction enzymes have been used in diagnostic medicine and molecular biology as well as genomics, genotyping, DNA diagnostics, molecular diagnostics and high throughput screening.

More recently, solutions to hybridization detection use labeled probes and/or targets that provide various optical or electrical signals when probes and targets hybridize. This type of technique has significant advantages over the above-described techniques that require complete chemical modification.

Other improved methods that use partial chemical modification are also known in the art. For instance, U.S. Pat. No. 5,591,578 to Meade et al., teaches the application of ruthenium complexes to the backbone of nucleic acid molecules. The ruthenium complexes are covalently bound to the ribose-phosphate backbone of the nucleic acid at predetermined positions. In addition, Lee (WO 99/31115 and Biochem. Cell Biol. Vol. 71, 1993, 162–168) teaches a number of techniques for hybridization detection using the electrical properties of M-DNA. However, each of these techniques, as well as others described in the literature, require modification of the probe as well as the sample used in the detection. In particular, the method of Lee et al. requires the use of more than one tag that has been chemically attached to the probe and/or target DNA for fluorescence detection. The need for the modification of the sample DNA is a common step for several of the hybridization detection techniques. The techniques require extensive sample preparation to obtain and modify DNA that works with these types of tests. Other disadvantages with the prior art concern detecting single base pair mismatches in the DNA after hybridization. In order to be able to detect such mismatches, very stringent conditions of pH, temperature and salt concentration must be maintained. (Jonathan A. Prince, Lars, Feuk, W. Mathias Howell, Magnus Jobs, Tesfai Emahazion, Kaj Blennow and Anthony J. Brookes, Genome Research, 11, 2001, 152–162) This often leads to high error rate in the detection of single base mismatches as in single nucleotide polymorphism (SNP) scoring.

Accordingly, there is an ongoing need for new inventions, methods and techniques that provide high signal and sensitivity during or after the hybridization process. These techniques should also have broad application to high throughput screening and microarray platforms. Furthermore, there is a need for a technique that is simple to use, needs minimal sample preparation and is capable of detecting single base pair mismatches using a simple hybridization procedure.

SUMMARY OF THE INVENTION

The invention provides an apparatus and method for detecting the presence of a target molecule.

The apparatus comprises a probe labeled with a transition metal-ligand complex for hybridizing with the target to form an initial complex, metal ions for doping the initial complex and forming a final complex, and potential means for providing a potential to the final complex to produce a detectable signal indicating the presence of the target.

The invention also provides a method for detecting the presence of a target molecule. The method comprises hybridizing a probe having an attached label to a target to produce an initial complex, adding metal ions to the initial complex to make a final complex, and applying a potential to the final complex to produce a measurable signal. In particular, the method of the invention teaches a technique wherein only a probe molecule needs to be tagged.

BRIEF DESCRIPTION OF THE DRAWINGS

Embodiments of the invention will now be described with reference to the drawings in which.

DETAILED DESCRIPTION OF THE INVENTION

Figure 1:
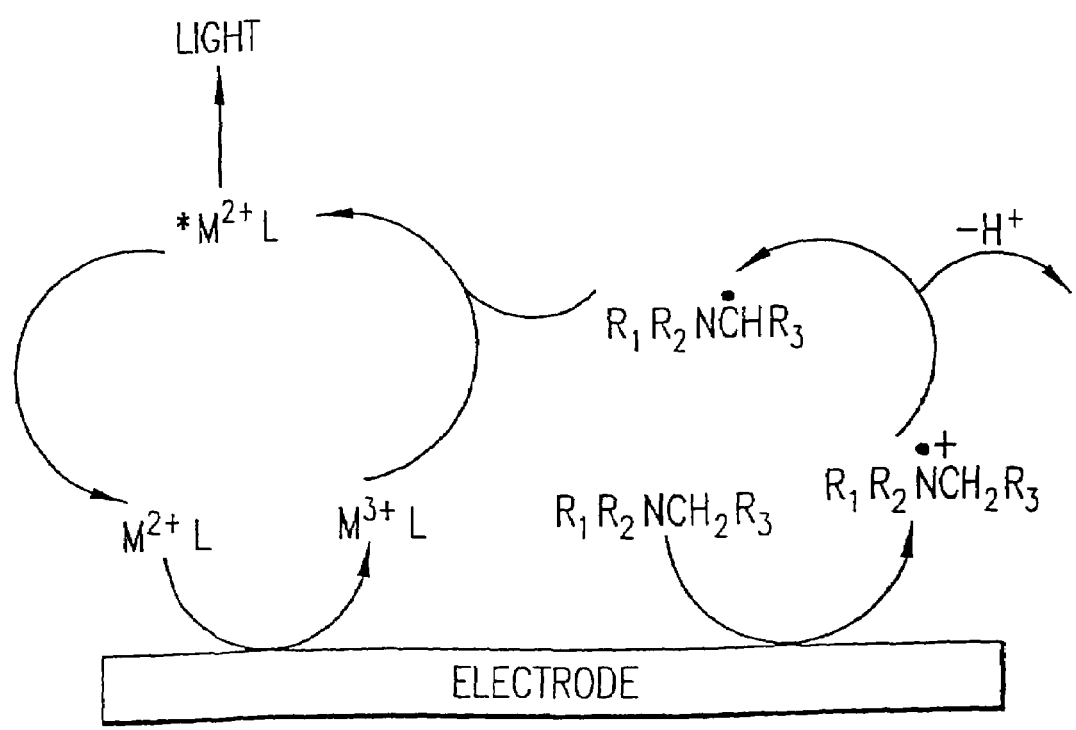
FIG. 1 shows a general schematic view of the chemistry of oxidation and reduction chemistry of the electrochemiluminescent compounds used with the present invention.

Before describing the present invention in detail, it is to be understood that this invention is not limited to specific compositions, process steps, or equipment, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the context clearly dictates otherwise. Thus, for example, reference to "a probe" includes more than one probe, reference to "a target" includes a plurality of targets and the like.

In describing and claiming the present invention, the following terminology will be used in accordance with the definitions set out below.

A "biopolymer" refers to a polymer of one or more types of repeating units. Biopolymers are found in biological systems and particularly include peptides and polynucleotides, as well as such compounds composed of or containing amino acid or nucleotide analogs or non-nucleotide groups. This includes polynucleotides in which the conventional backbone has been replaced with a non-naturally occurring or synthetic backbone, and nucleic acids in which one or more of the conventional bases have been replaced with a synthetic base capable of participating in Watson-Crick type hydrogen bonding interactions. Polynucleotides include single or multiple stranded configurations, where one or more of the strands may or may not be completely aligned with another. While probes and targets of the present invention will typically be single-stranded, this is not essential. Specifically, a "biopolymer" includes DNA (including cDNA), RNA and polynucleotides, regardless of the source.

A "nucleotide" refers to a sub-unit of a nucleic acid and has a phosphate group, a 5-carbon sugar and a nitrogen containing base, as well as analogs of such sub-units.

An "oligonucleotide" refers to a nucleotide multimer of about 10 to 100 nucleotides in length, while a "polynucleotide" includes a nucleotide multimer having any number of nucleotides.

A "biomonomer" refers to a single unit, which can be linked with the same or other biomonomers to form a biopolymer (for example, a single amino acid or nucleotide with two linking groups one or both of which may have removable protecting groups). A biomonomer fluid or biopolymer fluid refers to a liquid containing either a biomonomer or biopolymer, respectively (typically in solution).

The term "doping" refers to the process of adding at least one metal ion or other conductive molecule or material to a complex, nucleic acid, polymer or biopolymer. The term includes adding the metal ions to any part or component of the molecules or complexes. The metal ions or conductive molecules or materials need not be added between the molecules themselves, but may contact one or more of the molecules in some manner.

The term "transition metal ligand complex" refers to metal ligand complexes having centralized atoms from the transition metals of the periodic table. Transition metals include and are not limited to ruthenium, osmium, iridium etc.

The term "metal ion" refers to divalent and multivalent atoms. For example, nickel, zinc, cobalt. etc. Term also should be interpreted broadly to include elements and complexes from the lanthanide series of the periodic table. Metals have characteristic physical properties such as being efficient in conduction of heat and electricity, malleability, ductibility and a lustrous appearance. Chemically, metals lose electrons to form positive metal ions.

The term "initial complex" refers to a complex that contains at least one target and labeled probe. The complex may or may not be directly attached to a surface or substrate.

The term "final complex" refers to a complex that contains at least one metal ion, target, and labeled probe. The complex may or may not be directly attached to a surface or substrate.

The term "potential means" refers to any machine, device, or apparatus for adding a potential to the final complex. The term is intended to be broad based and include any and all circuitry whether chemical, electrical or mechanical that will provide a potential to the system and final complex. Other means and methods well known in the art are intended to be included in the definition.

The term "aptamer" refers to DNA or RNA molecules that have been artificially evolved and selected to bind other molecules, viruses, etc. They have many potential uses in medicine and biosciences technology.

The term "derivatives" refers to any molecule that can be produced directly from the molecule of interest using synthetic organic chemistry. Derivatives are synthesized molecules that have the original structure modified in some way through the addition or deletion of functional or non-functional groups.

An "array", unless a contrary intention appears, refers to any one or two-dimensional arrangement(s) of addressable regions bearing particular biopolymer moieties (for example different polynucleotide sequences) associated with that region. An array is "addressable" in that it has multiple regions of different moieties (for example, different sequences) such that a region at a predetermined location (an "address") on the array (a "feature" of the array) will detect a particular target or class of targets (although a feature may incidentally detect non-targets of the feature). In the present case, the polynucleotide (or other) target will be in a mobile phase (typically fluid), while probes for the target ("probes") may or may not be mobile (as described in this application). "Hybridizing" and "binding", with respect to polynucleotides, are used interchangeably. "Binding efficiency" refers to the productivity of a binding reaction, measured as either the absolute or relative yield of binding product formed under a given set of conditions in a given amount of time. "Hybridization efficiency" refers to a particular sub-class of binding efficiency, and refers to binding efficiency in the case where the binding components are polynucleotides. It will also be appreciated that throughout the present application, that words such as "upper", "lower" are used in a relative sense only. A "set" may have one type of member or multiple different types. "Fluid" as used herein refers to a liquid.

The term "target" refers to a nucleic acid, nucleotide, nucleoside or their analogs. The term shall also include nucleotides having modified sugars as well as organic and inorganic groups attached to the purine or pyrimidine rings. It shall be broad enough to include reference to RNA or modified RNA in gene expression detection.

The term "probe" refers to a nucleic acid, nucleotide, nucleoside or their analogs. The term shall also include nucleotides having modified sugars as well as organic and inorganic groups attached to the purine or pyrimidine rings.

It is to be understood that while the invention has been described in conjunction with the preferred specific embodiments thereof, the foregoing description as well as the example that follows are intended to illustrate and not limit the scope of the invention. Other aspects, advantages and modifications within the scope of the invention will be apparent to those skilled in the art to which the invention pertains.

FIG. 1 shows a diagram of how the electrochemiluminescence is produced using the chemistry of the present invention. ML is and abbreviation for the transition metal-ligand complex. M is an abbreviation for ruthenium or osmium. L stands for one or more ligands such as 2,2'-bipyridine or 1,10-phenanthroline. The electrode in the diagram is a working electrode that obeys standard properties known in the art (Yanbing Zu and Allen J. Bard, Anal. Chem., 72, 2000, 3223–3232). As can be seen in the diagram, the $M^{2+}L$ complex initially becomes oxidized at or near the surface of the working electrode to form the $M^{3+}L$ complex. Similarly, an amine is also oxidized at the surface of the electrode to form a cation radical. The amine cation radical is then deprotonated to form the carbon radical of the same compound by losing one proton. The carbon radical compound then donates an electron to the $M^{3+}L$ complex to form the excited state of this compound; shown as $*M^{2+}L$. This species then emits energy in the form of light (i.e. electrochemiluminescence is produced).

Figure 2:
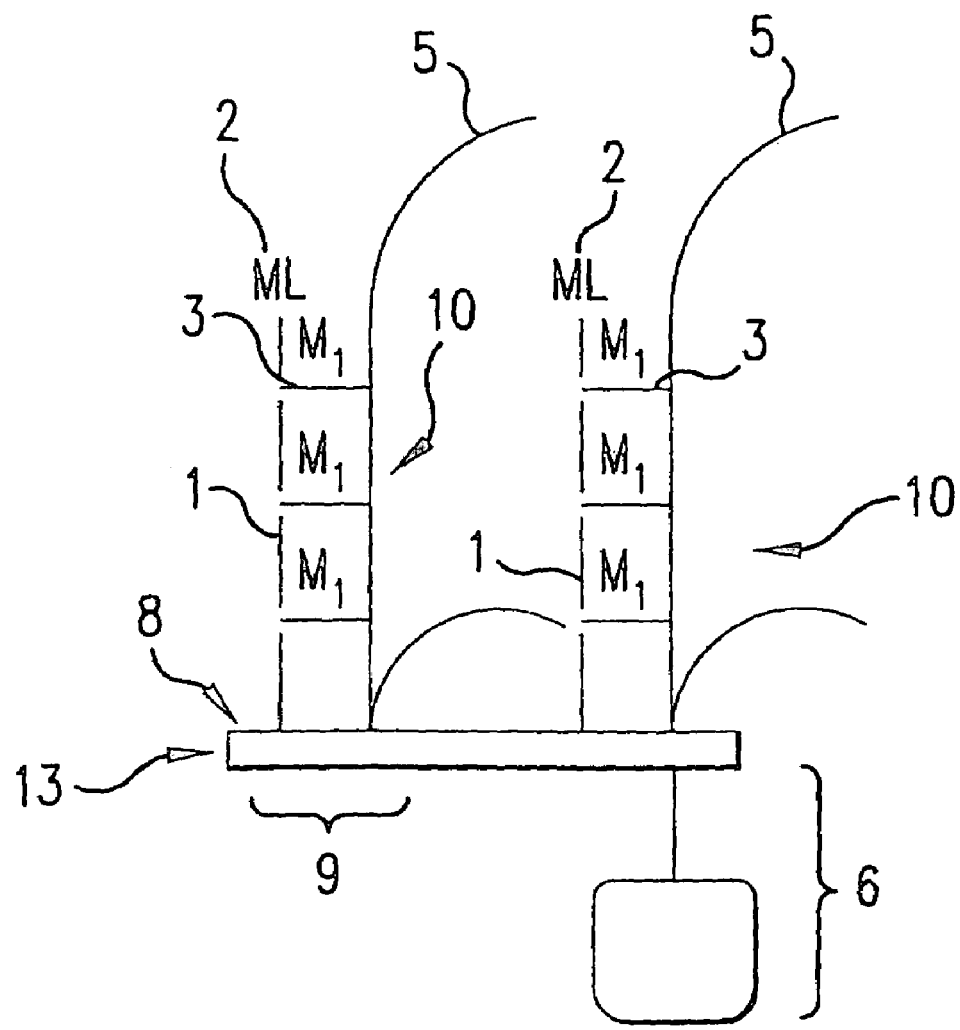
FIG. 2 shows a general schematic view of the apparatus of the present invention.

FIG. 2 shows a general diagram of the apparatus of the present invention. The invention provides an apparatus for detecting the presence of target 5. The apparatus includes a probe 1 labeled with a transition metal-ligand complex 2, a metal ion 3 for doping the hybridized probe 1 and target 5, and potential means 6 for providing a potential to the final complex 10. The linkage between DNA probe and transition metal-ligand complex can be based on the reactions of amino modified probes with NHS ester or isothiocyanate activated complexes, or vise versa. It can also be based on the reaction of thiol modified probes and maleimide activated complexes, or vise versa. The following references can be used as an example: (Ewald Terpetschnig, Jonathan D. Dattelbaun, Henryk Szmacinski and Joseph R. Lakowicz, Analytical Biochemistry, 251, 1997, 241–245; Gary F. Blackburn, Haresh P. Shah, John H. Kenten, Jonathan Leland, Ralph A. Kamin, John Link, Jeff Peterman, Michael J. Powell, Arti Shah, David B. Talley, Surendera K. Tyagi, Elizabeth Wilkins, Tai-Guang Wu and Richard J. Massey, clinical chemistry, 37(9), 1991, 1534–1539). The final complex 10 produces a detectable signal 7 (not shown in FIG.) from the transition metal-ligand complex 2. Probe 1 may be free in solution or attached to surface 8 by any well-known chemistry in the art. For instance, the probes can be deposited on the solid support via electronic statistic interactions, such as negatively charged DNA probes on a positively charged polylysine surfaces. The conjugation chemistry mentioned above for covalently linking probes and metal-ligand complexes can be applied to the deposition of probes. Another useful linkage is based on the reaction of thiol with gold to form Au—S bonds (J. S. Lee, WO 99/31115). Phosphoramidite chemistry may be used for directly attaching the probe 1 to the surface 8 (See FIG. 2) by the fast reaction between phosporamidite with hydroxyl. This technique is well known in the art. Attachment of the probe 1 may be accomplished by both covalent and non-covalent bonding methods. (Kazuhito Hashimoto, Masahiro Hiramoto, Tadayoshi Sakata, Hiroji Muraki, Hirofumi Takemura and Masamichi Fujihira, The Journal of Physical Chemistry, 91(24), 1987, 6198–6203).

The potential means 6 for providing the potential may include any number of devices or methods well known in the art. In particular, working electrode 13 (shown in FIGS. 2 and 3(A)–(C)) may be an anode or cathode for oxidizing or reducing electro-active components to the probe. This potential produces a detectable signal 7 from the transition metal-ligand complex 2 (signal 7 is shown in FIG. 3(C)), when the redox reaction is completed (details of the circuit or potential means 6 are not shown in the FIGS.). Potential means 6 may be any apparatus or device well known in the art for creating a potential (Mark M. Richter and Karen J. Brewer, Inorganic Chemistry, 32(13), 1993, 2827–2834). The potential means 6 may be applied to one or more of the final complexes 10. It is also within the scope of the invention that separate potential means 6 be applied to each feature 9 having one or more final complexes 10.

Figure 3A:
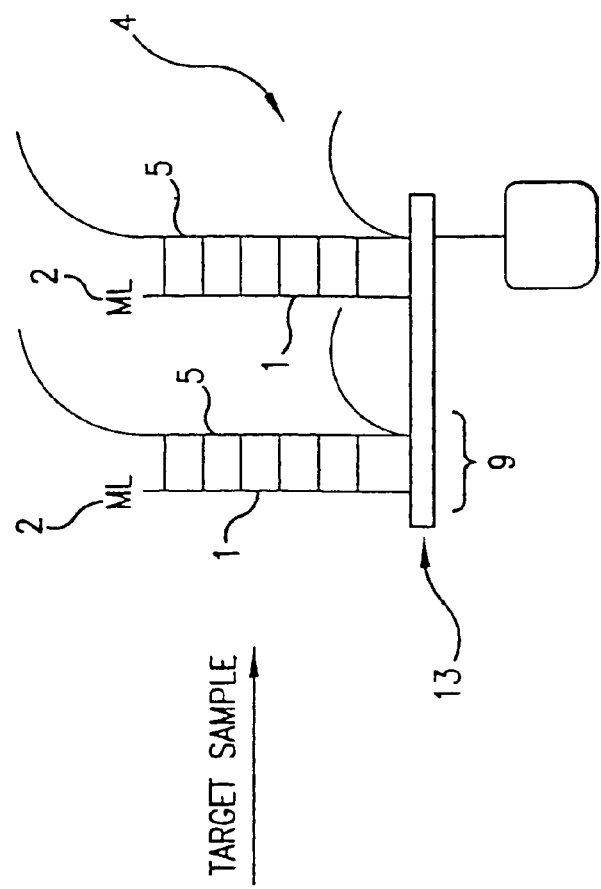
FIG. 3(A) shows a general schematic view of the invention with the probes bound to the electrode surface and the addition of the target to the probe to produce an initial complex.
Figure 3A:
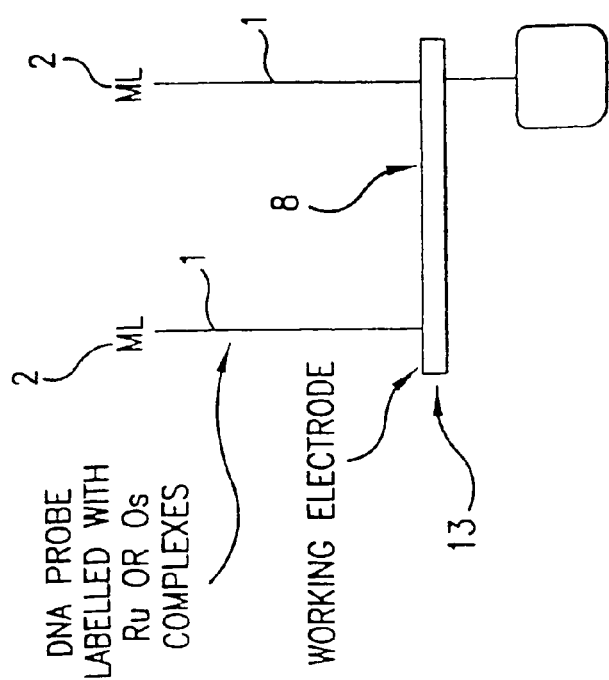
Figure 3B:
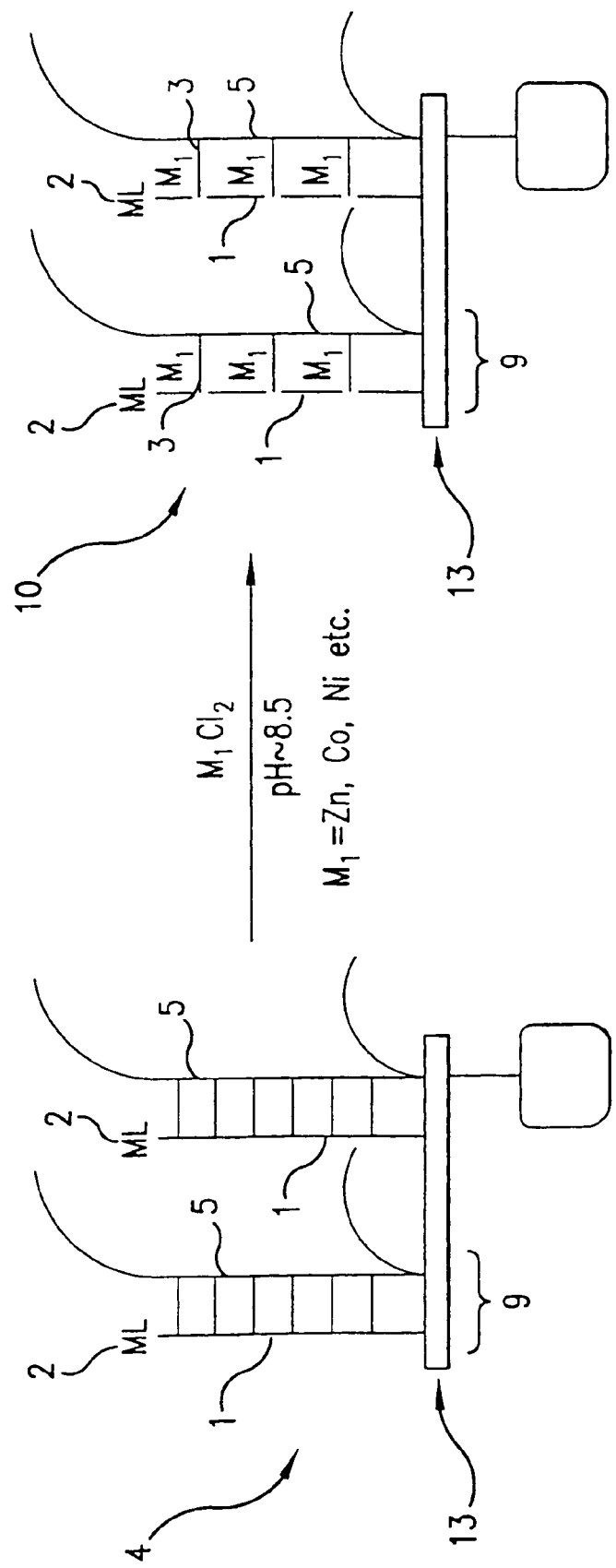
FIG. 3(B) shows a general schematic view of the invention after a target has hybridized to the probe and metal ions have been added to produce a final complex.
Figure 3C:
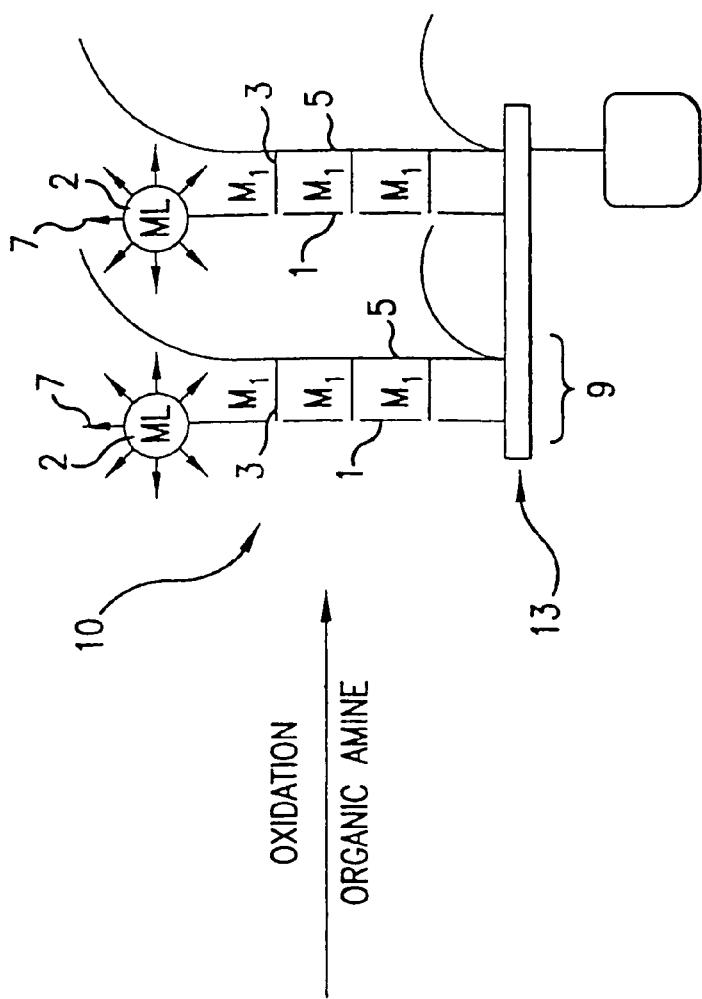
FIG. 3(C) shows a general schematic view when a potential is applied to the final complex to produce an electrochemiluminescent signal.
Figure 3C:
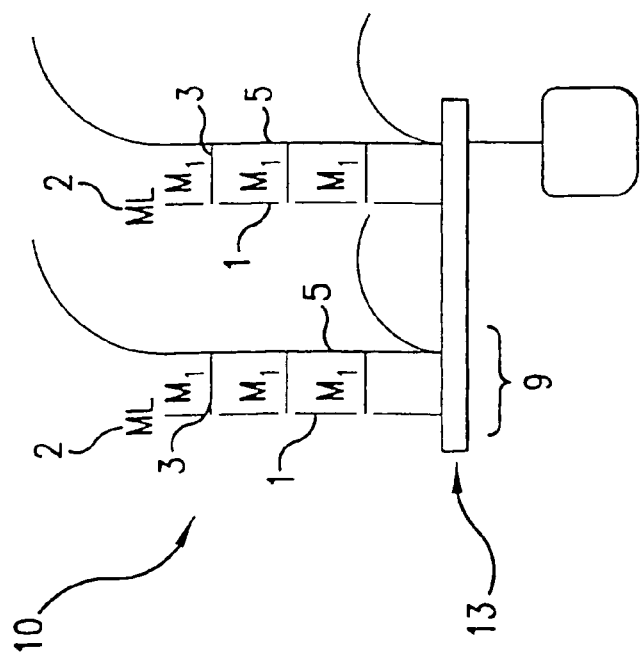

FIGS. 3(A)–(C) show the apparatus and method of the present invention. Probe 1 is labeled with a transition metal-ligand complex 2 and is attached to surface 8.

Surface 8 may include any number of materials, surfaces, biopolymers, biomonomers, oligonucleotides, proteins, amino acids chains, amino acids, aptamers, polynucleotides, co-polymers, or polymers capable of bonding to, attaching or binding nucleic acids or their derivatives. For example, surface 8 may be a microarray surface. In the case that surface 8 is a microarray surface, various features 9 can be designated and defined.

Probe 1 may include a variety of different types of nucleic acids, oligonucleotides, polymers, or aptamers. The important point being that probe 1 is designed for capturing or hydridizing to target 5. Probe 1 may be of a known or unknown sequence. Probe 1 is attached to surface 8 by chemical bonding such as covalent or non-covalent bonding. The probe 1 may be attached by any methods of attachment that are well known in the art.

Transition metal-ligand complex 2 is shown as (ML) in the diagram and is attached at the end of probe 1. Inorganic complex 2 may include any number of complexes capable of producing electrochemiluminescence upon oxidation. The ML used in the diagram represents ruthenium and osmium complexes with three 2,2'-bipyridine-like and/or 1,10-phenanthroline-like ligands (Yanbing Zu and Allen J. Bard, Anal. Chem., 72, 2000, 3223–3232). Other inorganic complexes may be used with the invention that are well known in the art. For instance, a number of inorganic complexes are disclosed in U.S. Pat. Nos. 6,140,138 and 6,048,687. The complexes and methods described in these patents as well as others described supra and infra are hereby incorporated by reference and may be used with the present invention.

Inorganic complex 2 may also include other metal ions, transition metals or alloys that are capable of providing chemiluminescent or electrochemiluminescent signals upon oxidation, reduction or excitation. The transition metal-ligand complex 2 may be attached to probe 1 in a variety of positions or orientations. For example, it may be linked to a DNA backbone ribose or phosphate. It may also be linked to a base or modified base (U.S. Pat. No. 5,591,578; Gary F. Blackburn, Haresh P. Shah, John H. Kenten, Jonathan Leland, Ralph A. Kamin, John Link, Jeff Peterman, Michael J. Powell, Arti Shah, David B. Talley, Surendera K. Tyagi, Elizabeth Wilkins, Tai-Guang Wu and Richard J. Massey, clinical chemistry, 37(9), 1991, 1534–1539). The diagram shows the label on the end portion of probe 1. This is the most convenient position, because it is easy to label and does not interfere with the bonding between the probe 1 and target 5.

It should be noted that target 5 may comprise any number of nucleic acids or polymers in various lengths and base pairs. Target 5 may be of known or unknown sequence.

FIG. 3(A) shows the addition of target 5 to the initial complex 4. If the target 5 is complementary to the probe 1, the strands hybridize to form the initial complex 4. Hybridization may be complete or partial depending upon the complementarity of the base pair sequences of target 5 and the probe 1.

FIG. 3(B) shows how the final complex 10 is constructed. A metal ion 3 is added to the initial complex 4 to form the final complex 10. The metal ion shown in FIG. 3(B) is in the form of a metal chloride. Metal ions with other counter ions may be used as long as the metal salts are soluble in water and solution can be maintained at a pH of 8.5. Slightly basic pH is used in order to allow the insertion of one divalent metal ion per base pair (Palok Aich, Shaunivan L. Labiuk, Les W. Tari, Louis J. T. Delbaere, William J. Roesler, Kenneth J. Falk, Ronald P. Steer and Jeremy S. Lee, J. Mol. Biol., 294, 1999, 477–485). This allows for the formation of highly conductive DNA. It is known in the art that the metals used in most cases will bond between base pairs in place of one hydrogen bond that would provide Watson-Crick base pairing between opposite nucleic acids strands. Metals include and are not limited to zinc, nickel, cobalt etc. The metal ion 3 must be capable of binding to the final complex 10. Under certain pH conditions, modification of bases can improve overall binding (Palok Aich, Heinz-Bernhard Kraatz and Jeremy S. Lee, Journal of Biomolecular Structure & Dynamics, Coversation 11, Issue #2, 297–301, Proceedings of the Eleventh Conversation, University of Albany, SUNY, Jun. 15–19, 1999; Personal Discussions.). For instance, this can be accomplished by replacing thymine with 5-fluorouricil in the probe and/or target.

FIG. 3(C) shows that upon the addition of an organic amine, the final complex 10 can then be used for detection of the target 5 by electrochemiluminescence. For instance, a potential is applied to the final complex 10 using the working electrode 13. The current is carried up the probe 1 and the target 5 after the metal ions have been inserted into the hybridized DNA to form a conductive wire. It should be noted that the transition metal-ligand complex 2 gets oxidized. As shown in FIG. 1, the application of the potential to the transition metal-ligand complex 2 results in electrochemiluminescence in the presence of the organic amine.

Figure 4:
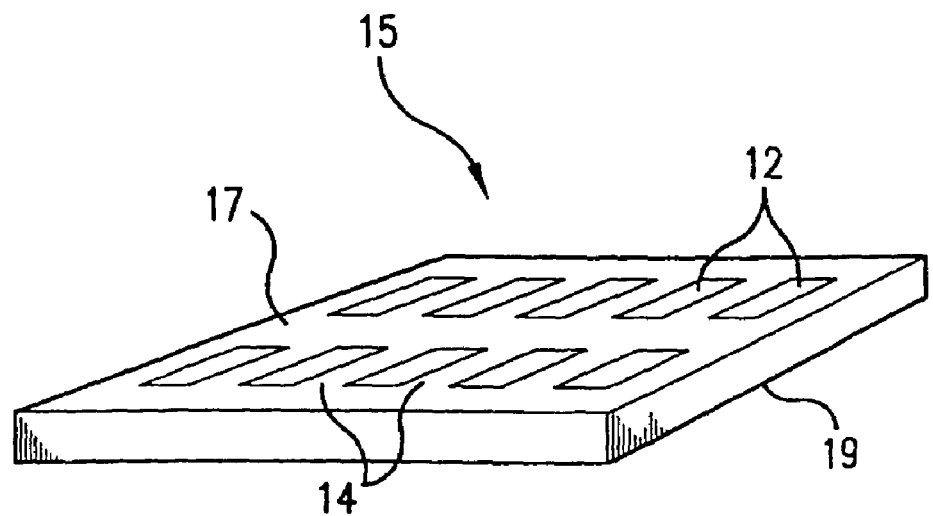
FIG. 4 shows the present invention as related to a microarray device.
Figure 5:
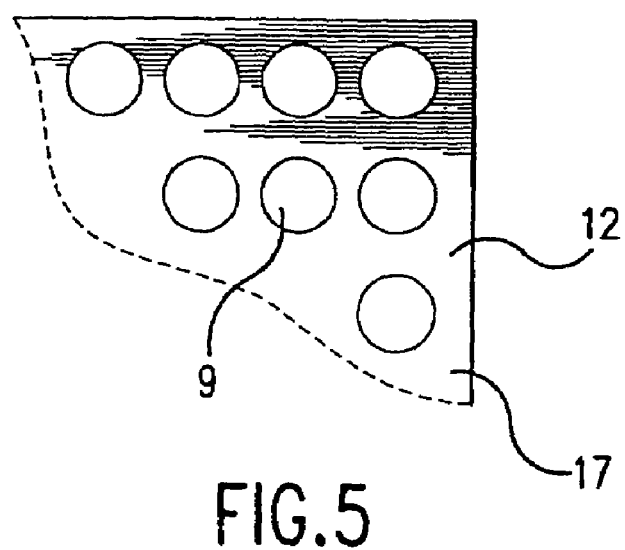
FIG. 5 shows an enlarged portion of the microarray device shown in FIG. 4.

FIGS. 4–5 show the present invention and how it relates to a microarray device 15. The microarray device 15 employs a first surface 17 on substrate 19 and separated by areas 14. Each microarray device 15 contains one or more features 9 used for detection of a particular target 5. Each feature 9 contains an apparatus as shown in FIG. 2 with one or more final complexes 10. Generally, a plurality of final complexes 10 will be present for each feature 9. This is done to increase the signal to noise ratio in the sample (i.e., a stronger electrochemiluminescent signal 7 will be provided). The invention can, therefore, be used for other applications such as gene expression and single nucleotide polymorphism (SNP) detection and mismatch detection.

Having generally discussed the present apparatus and method, a description of the method of the present invention and how it provides improved signaling and sequence mismatch detection is in order. As described, the method of the present invention operates by first hybridizing probe 1 with attached transition metal-ligand complex 2, to target 5 to form initial complex 4. Next, the initial complex 4 is made conductive by adding a metal ion 3 such as zinc, cobalt or nickel. Electrochemiluminescence is obtained by applying a potential to the final complex 10. The invention and method are particularly useful in that they effectively determine whether or not hybridization has taken place between probe 1 and the target 5, or one or more base pair mismatches exist. The highest signal can be obtained if there is a perfect match between probe 1 and target 5. It should be noted that divalent metal ions can not be inserted into the base pair(s) if the base pairs don't match. The conductivity of such M-DNA wire decreases dramatically. This will affect the oxidation rate of the final complex 10 and lowers the electrochemiluminescence signal. The magnitude of the signal can be used for determining the quantity and extent of binding or hybridization efficiency between the probe 1 and the target 5. The method thus can be applied to single mismatch/multi-mismatch detection.

EXAMPLE 1

Measurement and Detection

In order to obtain detection of the target, the following procedure will be employed. Target detection is accomplished in the final step after the target and the probe have hybridized. These steps have already been discussed in some detail. The method and apparatus for this detection will be briefly discussed here. A working electrode will be employed. In particular, the working electrode will be a gold electrode. A gold electrode is most effective for making the appropriate measurements for these types of experiments. In addition, gold electrodes are fairly effective reducing agents. However, this example should not be interpreted to limit the electrode to just gold. Other electrodes similar to gold may also be employed. Also, electrodes may comprise other materials and surface modification with carboxyl, amino, thiol and hydroxyl groups that are capable of reacting. The functional groups could be used to covalently link probes to the electrodes or other surface. The techniques are based on chemical reactions well known in the art of conjugation chemistry.

EXAMPLE 2

Attachment of Transition Metal-Ligand Complex to Probes

A number of methods known in the art may be used for attachment of the transition metal-ligand complexes to nucleic acids. The nucleic acids used in the experiment will be DNA. Other nucleic acids and oligonucleotides can be used. The DNA used as the probe in this experiment will be obtained from Promega, Inc. Probes that will be used will range in size from 1–100 oligonucleotides.

Initial targets will be produced using polymerase chain reaction of the known probe sequences. The cDNA or targets will be produced using an Amplicon oligonucleotide synthesizer following standard reaction sequences and procedures. cDNA will be purified from the reaction mix using a C13 reverse phase HPLC column. As discussed above, initial experiments will be conducted with known probe and target sequences to ensure hybridization. Further experiments will be conducted with genomic DNA digested with restriction endonucleases. In these experiments the probes will be of a known sequence that identifies a particular gene. Targets need not be of known size or sequence in these further experiments.

Attachment of the transition metal-ligand complexes to the probes should be straight forward. The example discussed below is one effective method of attaching the transition metal-ligand complexes to the probes. Other methods known and used in the art may also be employed. A terminal modified nucleic acid with a thiol functional group will be created on one end of the nucleic acid. The other end of the nucleic acid will contain an amino acid or amino functional group. The amino group will be reacted with NHS ester or isothiocyanate of a ruthenium complex at about pH 8.2–9.3. For more information on the steps and process see (Ewald Terpetschnig, Jonathan D. Dattelbaun, Henryk Szmacinski and Joseph R. Lakowicz, Analytical Biochemistry, 251, 1997, 241–245; Gary F. Blackburn, Haresh P. Shah, John H. Kenten, Jonathan Leland, Ralph A. Kamin, John Link, Jeff Peterman, Michael J. Powell, Arti Shah, David B. Talley, Surendera K. Tyagi, Elizabeth Wilkins, Tai-Guang Wu and Richard J. Massey, clinical chemistry, 37(9), 1991, 1534–1539). It should be noted that the actual preparation of the product can be produced either on solid phase or in solution. The desired product will then be obtained using a reverse phase HPLC column. Final products will be stored overnight in a −20° C. freezer.

EXAMPLE 3

Attachment of Probes to Substrate

The thiol terminated probes generated in example 2 above will be dissolved in an alcohol solution containing a gold electrode. The reaction will be allowed to proceed at ambient conditions for at least a couple of hours and probes will be deposited through Au—S bond formation.

EXAMPLE 4

Hybridization of Probes to Target

Although a number of conditions can be used for effectively hybridizing nucleic acids, the following method should prove most effective with the present invention. The hybridization of probe with target will be carried out at 20 mM Tris-HCl buffer at pH 7.5 at 37° C. in the presence of 10 mM NaCl for several hours. Incubation time and temperature will vary based on the length and composition of the probes.

EXAMPLE 5

M-DNA/Nucleic Acid Formation

The addition of the metal to the hybridized probe and target will be accomplished according to the following procedure. The formation of M-DNA will be carried out in CHES buffer at pH=9.0 in the presence of 0.1–0.2 mM $MCl_2$ (M=Zn, Co, Ni etc.). The reaction will be incubated for several hours depending on the probe length and composition. Additional information on methods and running conditions can be obtained from (Palok Aich, Shaunivan L. Labiuk, Les W. Tari, Louis J. T. Delbaere, William J. Roesler, Kenneth J. Falk, Ronald P. Steer and Jeremy S. Lee, J. Mol. Biol., 294, 1999, 477–485).

EXAMPLE 6

Electrochemiluminescence

Electrochemiluminescence (ECL) will be accomplished using the procedure discussed below. After hybridization and formation of the M-DNA, a potential will be applied to oxidize the ruthenium complexes in the presence of the organic amine. A number of organic amines well known in the art may be used. In particular, the tertiary amines are effective in producing ECL in most aqueous buffer systems. The ECL signal can be detected adjacent to the working electrode surface by a CMOS camera for array format or fluorimeters. It is expected that perfect match sequences will produce the highest signal for current or chemiluminescence detection due to the highest conductivity. Presence of mismatch base pairs should generate a reduced signal due to increase in resistance.

All patents and publications mentioned herein, both supra and infra, are hereby incorporated by reference.

We claim:

1. A kit for detecting the presence of a target, comprising:
   a nucleic acid probe that hybridizes to a target to form a first complex, the nucleic acid probe comprising a nucleic acid labeled with a transition metal ligand complex, and
   a free metal ion that binds to the first complex to form an electrically conductive second complex.

2. The kit of claim 1, wherein the second complex produces a signal when an electric potential is applied.

3. The kit of claim 1, wherein the metal ion is a divalent cation.

4. The kit of claim 3, wherein the metal ion is zinc, nickel or cobalt.

5. The kit of claim 3, wherein the metal ion is inserted between two bases of said complex.

6. The kit of claim 1, wherein the nucleic acid probe is bound to a solid support.

7. The kit of claim 6, wherein the solid support is an array.

8. The kit of claim 1, wherein the transition metal ligand complex at a terminus of the nucleic acid.

9. The kit of claim 1, wherein the transition metal ligand complex comprises ruthenium, osmium or derivatives thereof.

10. A system for detecting the presence of a target, comprising:
    a nucleic acid probe that hybridizes to a target to form a first complex, the nucleic acid probe comprising a nucleic acid labeled with a transition metal ligand complex;
    a free metal ion that binds to the first complex to form a second complex; and
    an electrode for providing a potential to said second complex to produce a detectable signal indicating the presence of the target.

11. The system of claim 10, wherein said signal is an electrochemiluminescent signal.

12. A nucleic acid complex having base pairs comprising:
    a nucleic acid probe comprising a nucleic acid labeled with a transition metal ligand complex;
    a target that is hybridized to said nucleic acid probe to form a complex; and
    a free metal ion that is inserted between base pairs of said complex.

13. A kit for detecting the presence of a target, comprising:
    a nucleic acid probe that hybridizes to a target to form a first complex, wherein the nucleic acid probe is attached to a substrate and comprises a nucleic acid labeled with a transition metal ligand complex, and
    a free metal ion that binds to the first complex to form an electrically conductive second complex.

14. A system for detecting the presence of a target, comprising:
    a nucleic acid probe that hybridizes to a target to form a first complex, wherein the nucleic acid probe is attached to a substrate and comprises a nucleic acid labeled with a transition metal ligand complex;
    a free metal ion that binds to the first complex to form a second complex; and
    an electrode for providing a potential to said second complex to produce a detectable signal indicating the presence of the target.

15. A nucleic acid complex having base pairs comprising:
    a nucleic acid probe comprising a nucleic acid labeled with a transition metal ligand complex, wherein the nucleic acid probe is attached to a substrate;
    a target that is hybridized to said nucleic acid probe to form a complex; and
    a free metal ion that is inserted between base pairs of said complex.

* * * * *